United States Patent [19]

Sogard et al.

[11] Patent Number: 6,139,573
[45] Date of Patent: Oct. 31, 2000

[54] CONFORMAL LAMINATE STENT DEVICE

[75] Inventors: David Sogard, Edina; Susan Shoemaker, Elk River; Jason Hill, Cottage Grove, all of Minn.; Bruce A. Parsons, Pompano Beach, Fla.

[73] Assignee: Scimed Life Systems, Inc., Maple Grove, Minn.

[21] Appl. No.: 09/035,501

[22] Filed: Mar. 5, 1998

Related U.S. Application Data

[63] Continuation-in-part of application No. 08/812,737, Mar. 5, 1997, abandoned.

[51] Int. Cl.$^7$ ....................................................... A61F 2/06
[52] U.S. Cl. ........................................... 623/1.13; 623/901
[58] Field of Search ............................. 623/1, 1.13, 1.11, 623/1.15, 1.16, 1.27; 606/108, 194

[56] References Cited

U.S. PATENT DOCUMENTS

| | | |
|---|---|---|
| 3,657,744 | 4/1972 | Ersek . |
| 4,300,244 | 11/1981 | Bokros . |
| 4,409,172 | 10/1983 | Ward, Jr. et al. . |
| 4,503,569 | 3/1985 | Dotter . |
| 4,580,568 | 4/1986 | Gianturco . |
| 4,604,762 | 8/1986 | Robinson . |
| 4,731,073 | 3/1988 | Robinson . |
| 4,732,152 | 3/1988 | Wallsten et al. . |
| 4,733,665 | 3/1988 | Palmaz . |
| 4,798,606 | 1/1989 | Pinchuk . |
| 4,816,339 | 3/1989 | Tu et al. . |
| 4,850,999 | 7/1989 | Planck . |
| 4,856,516 | 8/1989 | Hillstead . |
| 4,857,069 | 8/1989 | Kira . |
| 4,886,062 | 12/1989 | Wiktor . |
| 5,078,726 | 1/1992 | Kreamer . |
| 5,084,065 | 1/1992 | Weldon et al. . |
| 5,116,360 | 5/1992 | Pinchuk et al. . |
| 5,123,917 | 6/1992 | Lee . |
| 5,175,052 | 12/1992 | Tokuda et al. . |
| 5,282,824 | 2/1994 | Gianturco . |
| 5,330,500 | 7/1994 | Song . |
| 5,366,504 | 11/1994 | Andersen et al. . |
| 5,383,926 | 1/1995 | Lock et al. . |
| 5,389,106 | 2/1995 | Tower . |
| 5,443,499 | 8/1995 | Schmitt . |
| 5,474,727 | 12/1995 | Perez . |
| 5,507,771 | 4/1996 | Gianturco . |

(List continued on next page.)

FOREIGN PATENT DOCUMENTS

| | | |
|---|---|---|
| 0 539 237 | 4/1993 | European Pat. Off. . |
| 0 657 147 | 6/1995 | European Pat. Off. . |
| 1457 921 | 2/1989 | U.S.S.R. . |
| WO 95/05132 | 2/1995 | WIPO . |
| WO 95/29647 | 11/1995 | WIPO . |
| WO 96/00103 | 1/1996 | WIPO . |
| WO 96/03092 | 2/1996 | WIPO . |
| WO 96/10967 | 4/1996 | WIPO . |
| WO 96/22745 | 8/1996 | WIPO . |
| WO 96/26689 | 9/1996 | WIPO . |
| WO 96/35577 | 11/1996 | WIPO . |

OTHER PUBLICATIONS

Percutaneous Endovascular Graft: Experimental Evaluation by David D. Lawrence, Jr., M.D., Chusilp Charnsangavej, M.D., Kenneth C. Wright, Ph.D., Cesar Gianturco, M.D. Sidney Wallace, M.D., Radiology, May 1987, pp. 357–360.

*Primary Examiner*—David H. Willse
*Assistant Examiner*—Alvin Stewart
*Attorney, Agent, or Firm*—Hoffmann & Baron, LLP

[57] ABSTRACT

A method and apparatus for forming a covered endoprosthesis employs a conformed polymeric coating about an expandable stent. The expandable stent has an open tubular construction. A first polymeric liner is positioned about an inner surface of the tubular stent and a second polymeric liner is positioned about an outer surface of the tubular stent. The first and second polymeric liners are conformed to the tubular stent and laminated together through the open construction of the stent at a location coextensive with the inner surface of the tubular stent.

13 Claims, 7 Drawing Sheets

U.S. PATENT DOCUMENTS

| | | |
|---|---|---|
| 5,522,881 | 6/1996 | Lentz . |
| 5,562,697 | 10/1996 | Christiansen . |
| 5,591,195 | 1/1997 | Taheri et al. . |
| 5,653,697 | 8/1997 | Quiachon et al. . |
| 5,674,241 | 10/1997 | Bley et al. . |
| 5,700,285 | 12/1997 | Myers et al. . |
| 5,713,917 | 2/1998 | Loenhardt et al. . |
| 5,735,892 | 4/1998 | Myers et al. . |
| 5,749,880 | 5/1998 | Banas et al. . |

CONFORMAL LAMINATE STENT DEVICE

This application is a CIP of 08/812,737 Mar. 5, 1997 abandoned.

FIELD OF THE INVENTION

The present invention relates generally to an implantable intraluminal device. In its broadest aspect, the present invention relates to a composite intraluminal composite structure including a radially expandable stent having on one side a relatively smooth polymeric liner layer and on its opposite side having a conformal polymeric layer.

BACKGROUND OF THE INVENTION

It is well known to employ various endoprostheses for the treatment of diseases of various body vessels. One type of endoprostheses is commonly referred to as a stent. A stent is a generally longitudinal tubular device formed of biocompatible material which is useful to open and support various lumens in the body. For example, stents may be used in the vascular system, urogenital tract and bile duct, as well as in a variety of other applications in the body. Endovascular stents have become widely used for the treatment of stenosis, strictures or aneurysms in various blood vessels. These devices are implanted within the vessel to open and/or reinforce collapsing or partially occluded sections of the vessel. Often, stents may be used in conjunction with a graft with provides additional support for blood flow through weakened sections of the blood vessel.

Stents generally are open ended and are radially expandable between a generally unexpanded insertion diameter and an expanded implantation diameter which is greater than the unexpanded insertion diameter. Stents are often flexible in configuration, which allows them to be inserted through and conform to tortuous pathways in the blood vessels. The stent is generally inserted in a radially compressed state and expanded either through a self-expanding mechanism, or through the use of balloon catheters. For example, various stent constructions and their method of deployment are shown in U.S. Pat. Nos. 4,503,569 to Dotter; 4,733,665 to Palmaz; 4,856,561 to Hillstead; 4,580,568 to Gianturco; 4,732,152 to Wallsten and 4,886,062 to Wiktor. Published PCT Application No. PCT/US 95/08975, based on U.S. priority applications Nos. 08/282,181 and 08/457,354, also discloses a tubular shaped stent which is inflatable by balloon and which shrinks minimally in the longitudinal direction during expansion. The foregoing PCT publication and its U.S. priority applications, and the aforementioned U.S. patents are incorporated herein by reference. Additionally, published PCT Application WO 96/26689, entitled "Improved Longitudinally Flexible Expandable Stent" and being based on U.S. priority Application Nos. 08/396,569 filed Mar. 1, 1995 and 08/511,076 filed Aug. 3, 1995 also discloses stents useful in the present invention, both this PCT Application and its U.S. priority applications being incorporated by reference herein.

The attachment of stents to grafts for use in endovascular applications has generally been by means of sutures, cuffs or pockets in the graft which serve to house the stent. For example, U.S. Pat. No. 5,522,881 discloses cuffs on the exterior surface of the graft which serve as open pockets into which stents can be placed. It is known to attach stents to grafts using sutures. For the most part, grafts which are used in combination with stents as composite device have been made from textile materials, which are woven, knitted or braided.

Composite devices made from stents and films have been disclosed in the art. For example, U.S. Pat. No. 5,123,916 to Lee describes an expandable intraluminal vascular graft which includes concentric cylindrical tubes having a plurality of scaffold members mounted therebetween. The scaffold members are expandable, ring-like and provide circumferential rigidity to the graft.

U.S. Pat. No. 5,383,926 to Lock, et al. describes a radially expandable endoprosthesis which comprises an elongated sleeve member in which the radially outward expansion of the sleeve is limited by connecting strips. These strips are selectively removable to allow further outward expansion. The sleeve can be C-shaped in cross-section to allow for further expanded growth. The sleeve member generally has an open wall structure such as those typical of wire mesh tubing or slotted tubing. An expandable sheet material may be disposed across the open region of the C-shaped sleeve member and may be formed of Gortex®.

U.S. Pat. No. 5,389,106 to Tower discloses an impermeable expandable intravascular stent An impermeable deformable membrane interconnects portions of a distensible frame to form an impermeable exterior wall to the frame. The membrane is formed of a synthetic non-latex, non-vinyl polymer and the frame is made from a fine wire of annealed platinum. The distensible frame may be an expandable stent and the membrane is a hypoallergenic biologically inert material that is free of latex rubber proteins. The membrane should be impermeable and have the properties of elasticity, distensibility and barrier protection. No specific classes of materials are mentioned except the product name Tactylon®. The impermeable membrane is attached to the stent by dipping the stent into the polymer solution of the membrane and subsequently drying the device to remove the solvent. The stent is imbedded within the membrane surface.

With respect to grafts made from extruded materials such as expanded polytetrafluoroethylene (ePTFE), the use of sutures to attach such grafts encounters problems of dealing with bleeding through suture holes, since these expanded fluoropolymer materials do not generally have the self-sealing capability of elastomeric materials. Additionally, ePTFE is inherently resistant to adhesive bonding and few biocompatible adhesives will bond to its surface. While this inherent surface characteristic of ePTFE has advantages because it imparts a natural anti-thrombogenic characteristic to the surface of grafts made therefrom, it has been heretofore difficult to attach stents to grafts made from ePTFE without encountering the foregoing problems. The present invention seeks to overcome difficulties of attaching ePTFE material to a stent by using an anchoring material which can be carried into and entrapped in the porous surface of ePTFE.

In certain applications, it is necessary to protect against excessive cell growth through the stent (intimal hypoplasia), as well as thrombus formation and plaque build-up in the vascular system. In the bile or urogenital tract regions, tumor growth is also of concern. Additionally, arterial build-up of plaque and other debris can become dislodged from the vessel surface during or subsequent to implantation of the stent. To prevent such occurrences, the use of a cover or liner in combination with an ePTFE graft has been suggested by co-pending and co-assigned U.S. application No. 08/720, 091 filed Sep. 27, 1996, and entitled "Improved Covered Stent". This copending application is herein incorporated by reference. This copending application describes the use of unsintered ePTFE as a cover or liner used for a radially expandable stent. In the present application, a means of attaching such a cover or liner to a stent is provided.

An approach to preventing arterial buildup of plaque and other debris on an implanted stent has been discussed in co-assigned U.S. application No. 08/721,834, filed Sep. 27, 1996, entitled "Support Structure/Membrane Composite Medical Device". This co-pending application is herein incorporated by reference. This application describes the use of support member/membrane composite device which includes a support structure such as a radially expandable stent, a porous polymeric non-textile membrane adjacent to said support structure which defines an interface therebetween; and a thermoplastic anchor means attached to and extending from said stent into said porous polymeric non-textile membrane at the interface in order to anchor the membrane to the support structure.

Another such approach is disclosed in U.S. Pat. No. 5,700,285 to Myers et al. in which two tubes are adhered through the openings of a fully encased stent. The two tubes are shown to be adhered together midway through each stent opening. The covered stent is formed at a first diameter and is radially collapsible to a second smaller diameter for delivery to a site within a body lumen. The ability of the covered stent to recover to the first diameter provides sufficient compressive force against the vessel wall to hold the device in place. However, such a device presents slack in the outer stent covering when the device is recovered to a diameter that is less than the first diameter, i.e. the diameter at which the stent is formed.

In the present invention, an outer stent covering is adhered or otherwise affixed to an inner stent covering, i.e. a liner, at a location substantially coextensive with the inner stent surface. Adhering the coverings in this manner will minimize the disruption of the fluid contacting surface of the inner stent covering and thereby minimize the turbulence imparted to the fluid flowing therethrough. The present invention also teaches adhering the outer stent covering to the inner stent covering so as to maintain an airgap therebetween adjacent the stent structure and thereby provide domains of relatively high porosity for promoting neointima ingrowth. Furthermore, the present invention discloses a method for covering an expandable stent at a sub-nominal size in order to provide an expandable stent with a taut outer stent covering. As the sub-nominal covered stent is expanded to the nominal diameter for engaging a vessel wall, the outer stent covering will continue to have little or no slack, enhancing the compliance matching between the vessel wall and the pores of the outer covering. The sub-nominal size at which a device of the present invention is formed can be chosen for various vessel sizes having nominal given diameters.

In endovascular applications where the use of graft/stent combinations are increasingly important, recent studies have shown that at small diameters, e.g., 4 mm, grafts have not been successful in vivo. For example, both textile and polymeric grafts, i.e. PTFE grafts, when used alone suffer from kinking and radial collapse subsequent to implantation. When stents are used alone, that is without a graft, patency of the vessel is well maintained, but as mentioned above, excessive cell growth through the stent, as well as thrombus formation and plaque buildup is problematical. The present invention seeks to combine the advantages of a graft with those of a stent in a composite structure. The intraluminal composite structures of the present invention seek to provide the relatively smooth fluid-contacting surfaces of a graft with the structural support advantages of a stent. One objective of the present invention is to provide an intraluminal device which is particularly useful in small diameter applications, such as 4 mm diameter vessels, and which remains patent subsequent to implantation. Thus, the intraluminal composite devices of the present invention are designed to provoke a tissue response in the body that is normally encountered with a bare stent. This tissue response is one which promotes ingrowth and healing. The intraluminal devices of the present invention behave more like a stent than a graft, but have the advantages associated with the graft and can be used particularly well at the small diameter applications without suffering from the disadvantages associated with the individual use of a stent for a graft.

SUMMARY OF THE INVENTION

In one embodiment of the invention, the intraluminal device includes a composite structure having an elongate radially expandable tubular stent having an inner stent surface and an opposed external stent surface extending along a longitudinal stent axis, one of said surfaces having a conformal polymeric layer positioned thereon and the other of said stent surfaces having a polymeric liner layer positioned thereon. The polymeric conformal layer communicates through openings in the stent with the polymeric liner layer at a location coextensive with the inner stent surface. At these points of communication, the respective conformal and liner layers are fused or otherwise adhered together to form a laminate structure. In a preferred embodiment, the polymeric liner layer is positioned on the interior stent surface and is designed to provide a relatively smooth passageway for biological fluid, such as blood.

In another preferred embodiment, the stent is neither bonded nor adhered to the respective layers, but is firmly held therebetween. The respective layers sandwiching the stent can be peeled apart without demonstrating any noticeable adherance to the stent surface.

In another embodiment of the present invention, the composite intraluminal device includes an elongate radially expandable tubular stent having an interior stent surface and an opposed external stent surface extending along a longitudinal stent axis; a polymeric liner layer forming an inner surface on the interior stent surface to permit fluid flow therethrough; an external polymeric layer covering and conforming to the surface geometry of the external stent surface; and the polymeric liner layer and the external polymer layer being laminated together to form a composite structure containing the expandable tubular stent so as to form at least three domains of distinct porosity in the device.

In a further embodiment, the intraluminal composite device of the present invention includes an elongate polymeric tubular laminate structure having an elongate radially expandable tubular stent encased therein; said stent having an inner stent surface and an opposed external stent surface along a longitudinal stent axis; said laminate structure having an inner luminal surface for contacting fluid and an opposed external surface conforming to the contour of said external stent surface and defining laminate regions where said inner and external laminate structure surfaces are laminated to form an integral composite device.

In another embodiment of the present invention there is provided an elongate radially expandable tubular stent having an inner stent surface and an opposed external stent surface along a longitudinal stent axis; said stent being positioned within a polymeric tubular laminate structure; said laminate structure having an inner surface lining and an external surface conforming to the contour of said external stent surface and defining a laminate region wherein said inner surface and external surface of said laminate structure are fused.

In a further embodiment of the present invention an intraluminal prosthetic device is provided which includes an elongate tubular polymeric liner; an elongate tubular stent disposed over said liner, said stent having an open construction defined by stent segments and spaces therebetween; and a polymeric cover disposed over said stent and said liner, said stent cover being conformed to said stent segments and adhered to said liner through said spaces.

The polymeric liner layers and conformal layers may include a variety of polymeric materials, including fluoropolymers such as ePTFE and PTFE, polyimides, silicones, polyurethanes, polyurethane ethers, polyurethane esters, polyurethaneureas and the like, as well as mixtures and copolymers thereof. As discussed further herein, the stents may be fabricated from any number of useful materials and may be chosen from a variety of different stent structures and types. The preferred embodiment of the present invention includes a radially expandable tubular nitinol stent having an ePTFE polymeric liner disposed on the luminal surface of the tubular stent and having the conformal polymeric layer disposed on the external surface of the tubular stent.

The radially expandable stent may be chosen from a wide variety of stent materials and configurations. For example, the stent may be self-expandable, balloon expandable or made from a memory alloy, the configuration of which can be controlled by temperature.

The present invention further relates to a method of making an implantable intraluminal composite device, which includes the steps of providing a radially expandable tubular stent in the radially expanded state, applying a polymeric tubular liner or covering to either the luminal surface or the external tubular surface of the stent, further applying a conformal polymeric layer to the stent surface opposing the surface to which the liner layer is applied, providing sufficient pressure and heat to cause adherence of the layers together at their points of contact through openings in the stent at a location coextensive with surface of the stent. Alternatively, adherence of the respective layers can be accomplished by using an appropriate adhesive use of a solvent to soften or dissolve the surface of one or more of the layers and permit comingling of the layers which results in adherence. Other means of affixing the layers to one another are also contemplated.

An additional method of forming a covered intraluminal device of the present invention includes covering an expandable stent with an inner and outer layer of biocompatible material. The layers are laminated together through openings in the stent wall at a location coextensive with inner luminal surface of the stent. The lamination forms at least three distinct domains of porosity for promoting neointima ingrowth and preventing thrombus formation.

A further method of forming a covered intraluminal device of the present invention includes covering an expandable stent with an inner and outer layer of heat shrinkable material. The layers are laminated together through openings in the stent wall at a location coextensive with inner luminal surface of the stent. The stent is covered at a parent diameter that is greater than the diameter of the device during delivery but smaller than the diameter of the device when ultimately deployed in a vessel. The coverings are then heat shrunk to be taut about the stent at the parent diameters. For balloon expandable stents, heat shrinking of the coverings about the stent can be accomplished on a mandrel. If the stent is formed from a shape memory alloy which is designed to open at temperatures approximate to or greater than body temperature, a compressive force is generally required to hold the stent at the parent diameter until after the coverings have been heat shrunk and the stent has been cooled to a martensitic state.

A further method of the present invention for forming a composite endoluminal device includes the steps of providing an elongate mandrel, positioning a liner on said mandrel, and positioning an elongate expandable stent over said liner. The stent has an open structure defined by stent segments and spaces therebetween and including an inner stent surface and an outer stent surface. A cover is provided over said outer stent surface to thereby form a stent assembly on said mandrel which is them centered within the open expanse of a radially contractible tube such that both ends of said tube extend over said mandrel clear of said stent. One end of the radially contractible sleeve is contracted about the mandrel adjacent one end of the stent. The mandrel is then oriented so that the open end of said tube opens upward. The pocket is then filled with a flowable mass particulate. The tube is then radially contracted against the flowable mass particulate to push said cover into contact with said liner through said openings in said stent at a location coextensive with the inner stent surface. The cover is then laminated to said liner at said location coextensive with said inner stent surface.

A method of the present invention may further include providing a radially contractable sleeve formed of a heat-shrinkable material. Heat is applied to one end of said heat-shrinkable tube to shrink said tube to the diameter of said mandrel so as to form a pocket between said cover and said heat-shrinkable sleeve. Once the pocket is sufficiently filled with the flowable mass particulate, heat may then be provided to the heat-shrinkable tube to compress the flowable material against the cover. The flowable mass particulate thereby forces the cover through the openings in the stent and into contact with the liner.

A method according to the present invention may further include forming an intraluminal device using a mandrel having depressions or apertures formed on the surface thereof. The stent is positioned on the mandrel so that a portion of the openings of the stent are in registry with at least a portion of the depressions or apertures of the mandrel surface. Where the cover is forced through an opening in the stent that is in registry with a depression or aperture of the mandrel surface, the cover and liner will be compressed to a lesser extent than where the cover and liner are forced against the mandrel surface. The lower compression between the liner and cover at these locations will result in a fourth domain of distinct porosity. The fourth domain of distinct porosity exhibits an extent to porosity between the second and third domains of porosity described hereinabove.

A method according to the present invention may further include providing a liner or a cover which is formed from a material selected from the group consisting of fluoropolymers, polyimides, silicones, polyurethanes, polyurethane ethers, polyurethane esters, polyurethaneureas and mixtures and copolymers thereof. Additionally, the liner and said cover may be formed from ePTFE- Also, said heat-shrinkable tube may be formed from PTFE. When the liner and cover are formed of ePTFE the heating step desirably includes heating said stent assembly at a temperature below the sintering temperature of the liner and cover, or below about 327° C.

A method according to the present invention may further include positioning a stent formed of a shape-memory alloy and having a parent diameter corresponding to said liner positioned on said mandrel. The heating step would heat the stent at a temperature below that temperature used to set the shape memory of the stent. Further, said heating step may include applying a compressive force to said tube to maintain said stent at said parent diameter during said heating step. The stent is then cooled to a martensitic state and the compressive force is then removed.

DETAILED DESCRIPTION OF THE PREFERRED EMBODIMENTS

The present invention relates generally to a method and apparatus for providing a covering about an intermediate component having a complex open construction. The invention contemplates adhering, laminating, or otherwise bonding a fusible polymeric layer on either side of an open intermediate component and fusing the layers together to form a composite structure which functions essentially as a unitary member. It is contemplated that the fusion of the polymeric layers may be achieved by various techniques such as heat sealing, solvent bonding, adhesive bonding or use of coatings. The resultant composite structure would thereby include a complex open-construction, intermediate member being fully encased in lamination formed by the polymeric layers. The lamination would substantially surround the intermediate member closely following the contours of the complex geometry thereof. As will be described in further detail hereinbelow in a preferred embodiment of the present invention, the one or more laminants of polymeric material, preferably supplied in sheets, are positioned about the intermediate member. Pressure is used to compress against one surface of the intermediate member forcing the laminate to conform to the open configuration of the intermediate member. Once so conformed, fusion is effected between the layers, with the fusion occurring within the open spaces defined by the open construction at a location coextensive with the inner surface of the intermediate member.

The present invention is particularly suitable for forming an endoluminal prosthesis for vascular applications. An expandable stent is encased in multiple layers of a polymeric material preferably expanded polytetrafluoroethylene (ePTFE). The ePTFE layers are fused together through the open construction of the stent so that the covered stent exhibits a relatively smooth surface as compared with an uncovered stent. Such a smooth stent has a tendency to reduce thrombotic formation after vascular implantation and to impart less turbulence to the fluid flowing therethrough.

Figure 1:
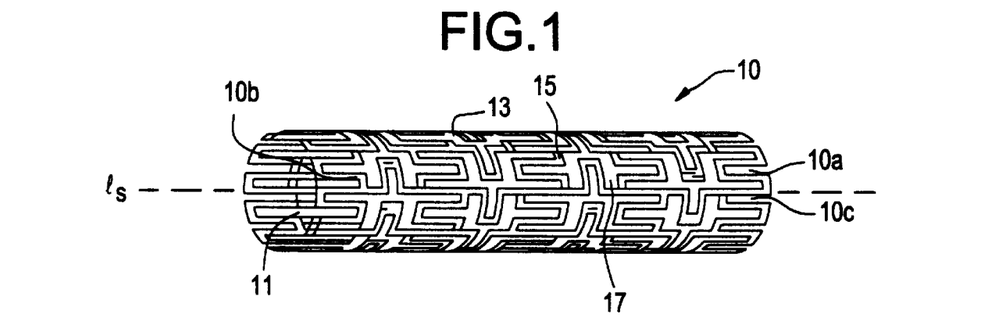
FIG. 1 is a perspective showing of a stent of the type which may be used in combination with the composite endoprosthesis of the present invention.

Referring now to the drawings of the present application, FIG. 1 shows a stent which may be employed in combination with the present invention. Stent 10 is generally an elongate tube having a longitudinal stent axis $I_S$. Stent 10 has opposed open ends 10a and 10b and a central lumen 10c therebetween. The body of stent 10 defines an interior surface 11 and an opposed exterior surface 13. The stent is formed to have a generally open configuration having a plurality of passages or openings 15 through solid portions 17 of the body. These openings 15 provide for longitudinal flexibility of the stent as well as to permit the stent to be radially expanded once deployed in a body lumen such as a blood vessel.

The polymeric liner and conformed layers of the present invention may be formed by a variety of methods. For example, extrusion processes such as ram extrusion; polymeric casting techniques such as solvent casting and film casting; molding techniques such as blow molding, injection molding and rotational molding; and other thermoforming techniques useful with polymeric materials may be employed and chosen to best serve the type of material used and specific characteristics of the liner or cover desired.

While either or both of the polymeric liner and conformal layer may be provided directly in tubular form, i.e as an extruded tube, either one or both can also be formed from extruded sheets of material which can be wrapped around all or a portion of the stent to form a cover or liner. Combinations of sheets and tubes are also contemplated. For example, in one embodiment a sheet may be first formed and wrapped externally about the stent and seamed along the longitudinal axis to form a cover. Such a sheet may be made with a high degree of uniaxial orientation. The relative axis of orientation of the stent may vary depending on the material used to form the liner or cover and the orientation and size of its pore structure. For example, in applicants' aforementioned copending U.S. application No. 08/721,834, the extruded material used to form the liner or cover may be formed from unsintered ePTFE sheets which have been expanded longitudinally and aligned generally longitudinally along the longitudinal stent axis, transverse to the longitudinal direction, or in an off-axis angle therebetween. In another example, a sheet or tube of ePTFE may be stretched and sintered several times to create a preformed ePTFE having expansion memory, such as shown in PCT Publication No. WO 96/00103 (U.S. patent application No. 95/07326), which is herein incorporated by reference. This publication is based on U.S. priority application 08/265,794, filed Jun. 27, 1994, which is also herein incorporated by reference. The preformed ePTFE allows for further expansion once the stent is implanted and radially deployed. Other embodiments of the present invention include the use of one or more tubes, providing a tube and a sheet formed into a tubular structure, or providing a plurality of sheets formed into a tubular structure on either surface of the stent.

As previously mentioned, the support structure of the composite device may be chosen from a wide variety of materials and configurations. Endovascular stents are the preferred support structure and may be formed in a wide variety of configurations. An example of a useful stent in the present invention is shown in FIG. 1. This particular stent represents a slotted tubular stent which is designed to radially expand either by balloon catheter or by forming the stent from a temperature-sensitive memory alloy which changes shape at a designated temperature or temperature range. Other stent types, such as tubular-shaped wire stents and self-expandable spring-biased stents are also contemplated. The stent may be made from a variety of materials including stainless steel, titanium, platinum, gold and other bio-compatible metals. Thermoplastic materials which are inert in the body may also be employed. Shaped memory alloys having superelastic properties generally made from specific ratios of nickel and titanium, commonly known as nitinol, are among the preferred stent materials.

Various bioeffecting agents may also be included in the polymeric cover or liner by well known methods. For example, anti-infective agents and/or antithrombogenic agents may be coated on the polymeric cover or conformal layer or disposed within some of the pores of the polymeric cover or conformal layer prior to implantation. Additionally, such bioeffecting agents may also be employed on the stent or in the anchoring material used thereon. One example is shown in commonly assigned International Patent Application No. WO 95/29647, published on Nov. 9, 1995 and its U.S. priority applications Ser. No. 235,300, filed Apr. 29, 1994, and Ser. No. 350,233, filed Dec. 1, 1994, which are incorporated herein by reference.

A preferred stent of the present invention is of the type more fully shown and described in International Patent Application No. WO 96/03092 A1, published on Feb. 8, 1996, which along with its priority U.S. patent applications, Ser. No. 08/282,181, filed Jul. 28, 1994, and Ser. No. 08/457,354, filed May 31, 1995, are incorporated by reference herein. This stent is also shown in the above incorporated patent applications bearing U.S. application Nos. 08/720,091 and 08/721,834. The stent shown in these incorporated documents has a patterned shape including a first and second meandering patterns extending orthogonally to each other. The particular meandering pattern and the opening or spaces therebetween allow the stent to be easily deployed through curved blood vessels as it renders the stent longitudinally flexible. Furthermore, the particular configuration of stent 10 shown herein allows the stent to be radially expanded without significant reduction in longitudinal expanse.

Figure 2:
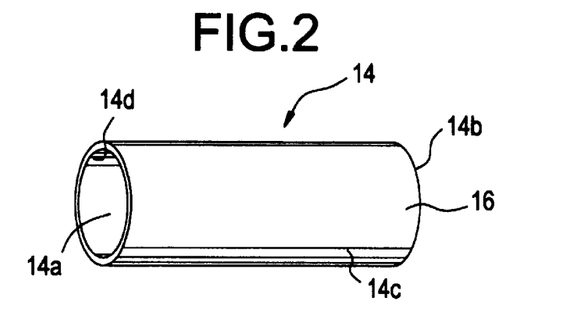
FIG. 2 is a perspective view of a tubular liner used in combination with the stent shown in FIG. 1.
Figure 3:
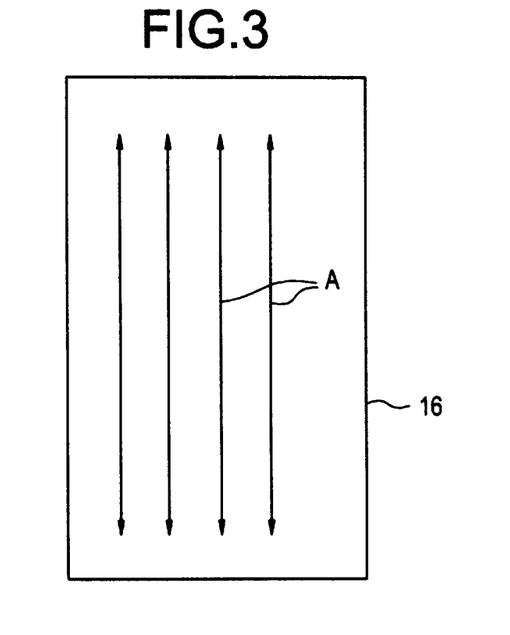
FIG. 3 is a plan view of a planar polymeric sheet used to form the liner of FIG. 2.

Referring additionally to FIG. 2, in order to provide the covered stent construction of the present invention, stent 10 may be employed in combination with an inner tubular liner 14. Inner tubular liner 14 may be formed of any suitably biocompatible polymeric material. In the present illustrative embodiment, it is preferred that liner 14 be formed of expanded polytetrafluoroethylene (ePTFE) as this material is well-known for use in implantable vascular applications. Inner tubular liner 14 may be formed by any process well-known in the PTFE forming art. However, in the preferred embodiment of the present invention, inner tubular liner 14 is formed from a planar sheet 16 of ePTFE such as shown in FIG. 3. Planar sheet 16 desirably includes pores between about 2 and 10 microns in size. The use of a planar sheet 16 of ePTFE to form tubular liner 14 permits the beneficial use of the expansion properties of extruded sheets or films. These sheets or films tend to be highly uniaxially oriented in the extrusion or machine direction (arrows A). However, such extruded sheets exhibit substantial expansion capabilities in a direction perpendicular to the machine direction. By forming inner tubular liner 14 of a rolled sheet 16 of extruded material, maximum advantage can be taken of the inherent expansion capabilities of such extruded materials. Thus, as will be described in further detail hereinbelow, as the stent 10 is designed for substantial radial compliance, inner tubular liner 14 so formed will readily expand and contract with the stent.

Figure 4:
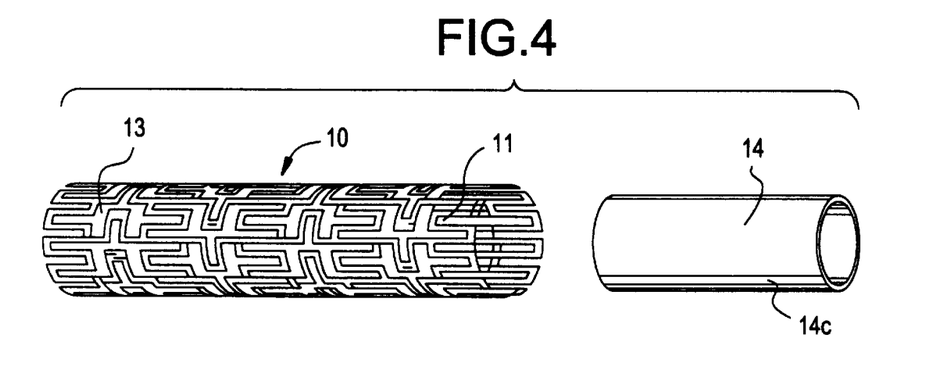
FIG. 4 is a perspective showing of the stent of FIG. 1 and the inner liner of FIG. 2.

Referring again to FIG. 2, liner 14 is generally a tubular member having opposed open ends 14a and 14b, an outer stent contacting surface 14c and an inner luminal surface 14d. Inner tubular liner 14 generally has a length which corresponds to the length of stent 10. Inner tubular liner 14 is constructed to have an outer diameter which is approximately equal to the inner diameter of stent 10 so that the inner liner 14 may be placed internally of stent 10 with the outer stent contacting surface 14c thereof in intimate contact with the interior surface 11 of stent 10 in a manner depicted in FIG. 4. Thus the inner surface 11 of stent 10 is covered or coated by liner 14.

Figure 5:
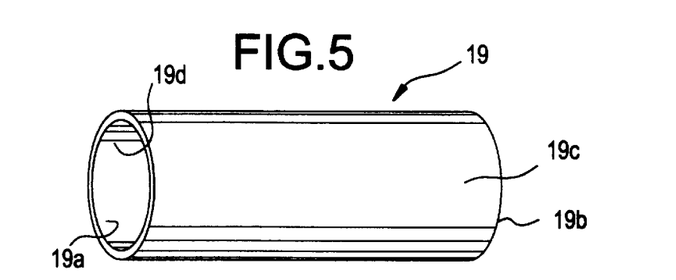
FIG. 5 is a perspective showing of a tubular outer liner used in combination with the stent of FIG. 1.

Turning now additionally to FIG. 5, the outer surface 13 of stent 10 may be covered by a liner-type polymeric coating or cover 19 preferably also formed of ePTFE. The outer coating or cover 19 may be applied by various techniques. The outer coating or cover 19 may be formed separately and then applied to the outer surface of stent 10 or the coating or cover may be formed directly thereover. Various coating techniques may be used to apply the cover directly thereto. One preferred technique to apply a cover or coating to the exterior surface of the stent is to form an ePTFE outer tubular liner or cover 19 thereover.

Figure 6:
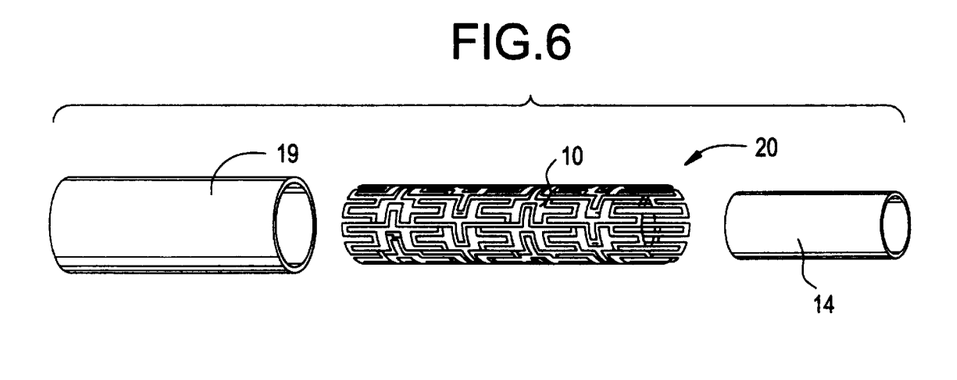
FIG. 6 shows an exploded perspective view of assembled outer tubular liner of FIG. 5, the stent of FIG. 1 and the inner tubular liner of FIG. 2.

With reference to FIG. 5, outer tubular liner 19 may be formed in a manner substantially similar to inner tubular liner 14 described above with respect to FIG. 2. Outer tubular liner 19 has a length which is substantially equal to the length of stent 10 having opposed ends 19a and 19b. Outer tubular liner 19 further includes an outer tubular surface 19c and an inner stent contacting surface 19d. As with inner tubular liner 14, outer tubular liner 19 may be preferably formed from an extruded sheet of ePTFE (such as shown in FIG. 3) rolled into tubular configuration shown in FIG. 5. It is further contemplated that outer tubular liner 19 may be constructed to have an inner diameter which is approximately equal to the outer diameter of stent 10 so that the outer tubular liner 19 may be fitted in intimate relationship thereover. It is also contemplated that outer tubular liner 19 may be formed by wrapping the planar sheet directly about the exterior surface of stent 13. Thus as shown schematically in FIG. 6, a composite tubular endoprosthesis 20 is formed by combining an open construction stent 10 between an inner tubular liner 14 and an outer tubular liner 19.

It is contemplated by the present invention that each of inner tubular liner 14 and outer tubular liner 19 may be formed of one or more sheets or tubes or combinations of one or more sheets and one or more tubes. Furthermore, each of inner tubular liner 14 and outer tubular liner 19 are desirably formed to be extremely thin, the thickness of each being limited only by the limitations of practical processing. Each of inner tubular liner 14 and outer tubular liner 19 desirably have a thickness of about 0.025 millimeters or less and present a combined thickness of less than 0.05 millimeters when laminated together through the openings 15 in stent 10.

Figure 7:
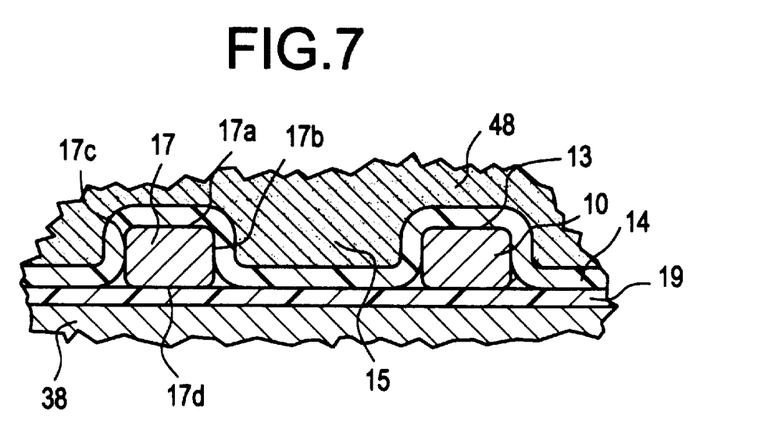
FIGS. 7 and 8 are cross-sectional views of different embodiments of the present invention showing the outer tubular liner and inner tubular liner enclosing the stent.
Figure 8:
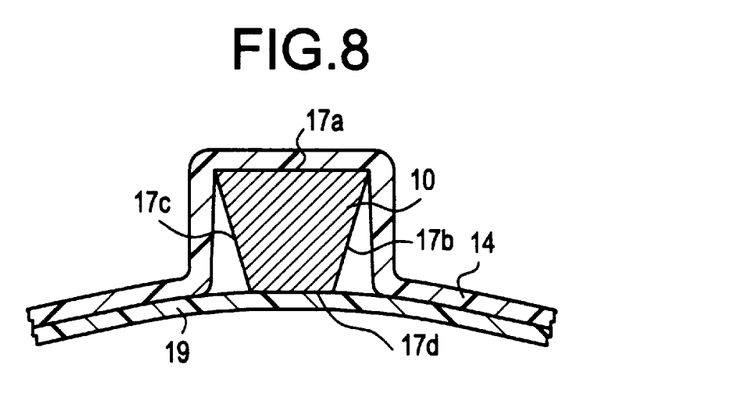

With additional reference to FIGS. 7 and 8, inner tubular liner 14 and outer tubular liner 19 are shown encasing the solid portions 17 of tube 10. With reference to FIG. 7, liners 14 and 19 substantially cover the solid portions 17 of stent 10. This results in the outer tubular liner 19 coating an upper surface portion 17a of solid portion 17 as well as a substantial extent of depending opposed side surface portions 17b and 17c thereof. An opposed lower surface portion 17d of the solid portions 17 is coated by inner tubular liner 14. FIG. 7 shows surface portions 17a–17d of stent 10 covered by liners 14 and 19 and being substantially coated. However, as shown in FIG. 8 it is only necessary to enclose or envelope the surface portions 17a–17d of stent 10 with liners 14 and 19. In the embodiment shown in FIG. 8, upper and lower surface portions 17a, 17b are coated by liners 14 and 19 respectively and opposed side portions 17b and 17c are enclosed thereby.

Figure 9:
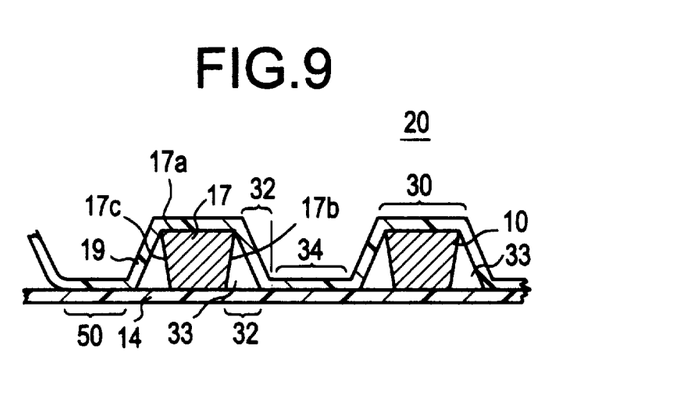
FIG. 9 is a partial cross-sectional view of the invention of FIG. 8 showing the formation of the domains of distinct porosity.

FIG. 9 illustrates the provision of at least three domains of distinct porosity by a device of the present invention shown in FIG. 8. A first domain of porosity 30 is formed at a stent segment between liner 14 and cover 19 and has a first porosity. A second domain of porosity 32 is formed by liner 14 and cover 19 adjacent to a stent segment 17 and has a second porosity greater than the first porosity. A third domain of porosity 34 is formed by liner 14 adhered to cover 19 between adjacent stent segments and has a third porosity between the first and second porosities. The porosity of third domain 34 correlates to the bulk density provided by liner 14 and cover 19 in that it bears the full force of compaction during formation of endoprosthesis 20. Referring still to FIG. 9, a method according to the present invention may further include forming an intraluminal device of the present invention having a fourth domain of distinct porosity 50 exhibiting a porosity between the second and third porosities described hereinabove.

Figure 10:
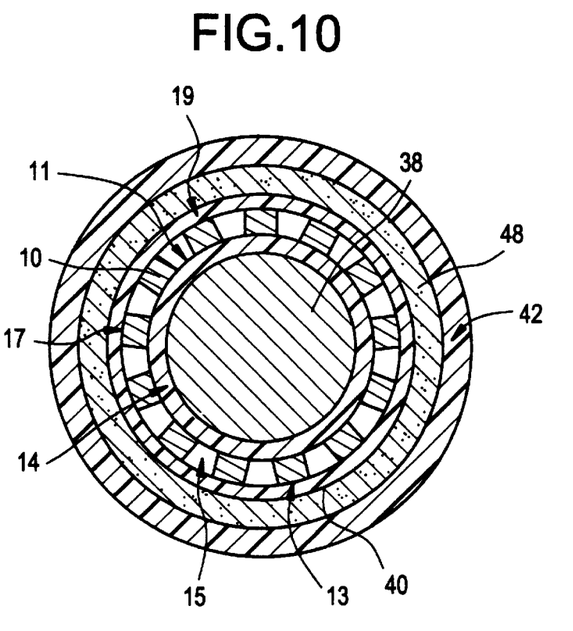
FIGS. 10 and 11 show steps in forcing the outer tubular liner of FIG. 5 through openings in the stent of FIG. 1 to make contact with the inner tubular liner of FIG. 2.
Figure 11:
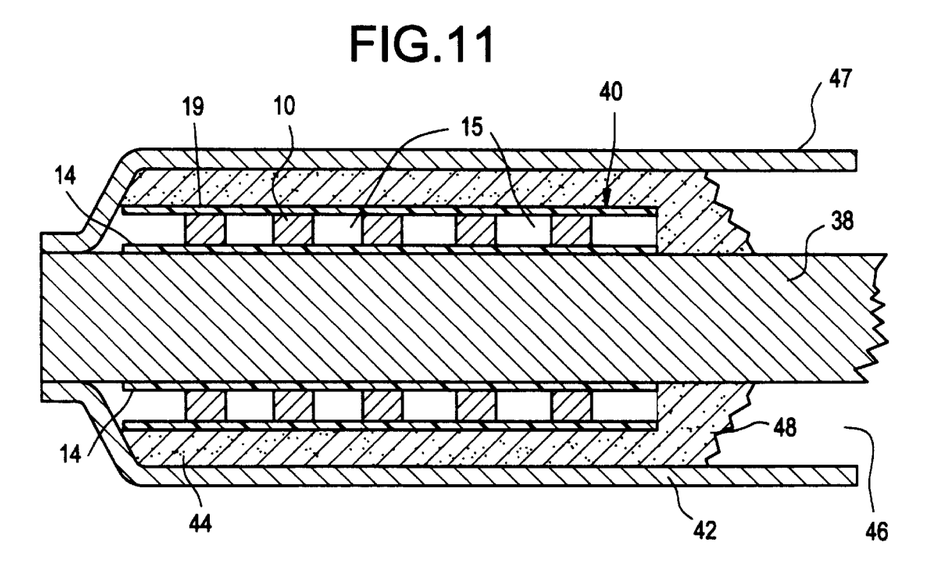

Referring to FIGS. 10 and 11, a method of forming a composite endoluminal device of the present invention includes the steps of providing an inner liner 14 on an elongate mandrel 38. An elongate expandable stent 10 having a cylindrical body and defining an interior surface 11, an exterior surface 13, and having openings 15 therethrough is then positioned over inner liner 14 and engaged thereto. An outer stent cover 19 is positioned over stent 10 to form a stent assembly 40 including inner liner 14, stent 10, and outer stent cover 19. Outer stent cover 19 is compressed through openings 15 of stent 10 and into contact with inner liner 14. Cover 19 is adhered or otherwise laminated or bonded to liner 14 at a location substantially coextensive with interior surface 11 of stent 10. The present invention also contemplates heating stent assembly 40 while still on mandrel 38 to heat shrink cover 19 and liner 14 about stent 10.

It is contemplated by the present invention that the location coextensive with interior surface 11 of stent 10 generally includes an area slightly interior of interior surface 11 where cover 19 is compressed fully through an opening 15. It is also contemplated that the location coextensive with interior surface 11 of stent 10 generally includes an area slightly exterior of interior surface 11 within opening 15 where stent 10 is itself compressed upon inner liner 14 so that uncompressed portions of liner 14 may break the plane of interior surface 11 by extending into opening 15. It is further contemplated once the compression force is released after cover 19 is adhered to liner 14, the compressed cover 19 may tend to relax in a manner that pulls liner 14 at least partially into opening 15 so that the interface between liner 14 and cover 19 is positioned within opening 15.

The method of forming a composite intraluminal device of the present invention may include laminating, adhering, or bonding cover 19 to liner 14 in a manner that cover 19 fully conforms to the complex geometry provided by the exterior surface 13 and the openings 15 of stent 10, as shown in FIG. 7. While the device of FIG. 7 would substantially reduce or eliminate the formation of a domain of porosity including an air gap-between cover 19 and liner 14, such a device exhibits substantial benefits in endovascular use as the entire stent is covered with a biocompatible thrombus inhibiting material which encourages tissue ingrowth and maintains metabolic communication across cover 19 and liner 14. Furthermore, as the inner luminal surface of the endoprosthesis is formed against a smooth mandrel, the inner luminal surface of the composite endoprosthesis exhibits a relatively smooth configuration mitigating against turbulent blood flow and thrombus formation during use.

The step of compressing cover 19 to contact liner 14 is desirably performed by forcing a flowable mass against cover 19 so as to force-cover 19 through openings 15 of stent 10. The flowable mass is desirably formed from a flowable particulate such as granules or grains of salt, and or other material capable of transmitting a compaction force fluidly and substantially uniformly to the contour of the stent. The flowable particulate is desirably capable of withstanding temperatures which permit conformation of the cover about and through the openings of the stent and fuse the cover to the liner therethrough. Most desirably, the particulate flowable mass is water soluble to facilitate removal of particles during washing steps in the manufacturing and assembly process. In one embodiment, the particulate flowable mass is formed by a composition including sodium chloride. The composition may also include an anticaking agent or flow aid, such as tricalcium phosphate and the like.

The composite intraluminal device of the present invention is formed so as to define at least three domains of distinct porosity as shown in FIG. 9. Each domain of porosity provides distinct characteristics for permitting neointima ingrowth into the device and result in assimilation of the device by the vessel. A first porosity domain 30 is formed where the liner 14 and cover 19 each come in contact with stent 10 at stent surface portions 17a and 17b. The porosity of the first domain 30 is relatively low since the stent surface is a barrier to substantial neointima ingrowth. The second domain of porosity 32 formed by liner 14 and cover 19 adjacent to the stent side surface portions 17b or 17c and spanning air gap 33 generally maintains the respective porosities of cover 19 and liner 14 as originally provided or as may be expected after a heat shrinking step. A third domain of porosity 34 is formed where liner 14 is laminated, adhered, or bonded to cover 19. The porosity of third domain 34 correlates to the bulk density of liner 14 and cover 19 in that it bears the full force of compaction of the flowable mass particulate. The relative size of the second domain of porosity 32 and the third domain of porosity 34 may be controlled by selecting the amount of compressive force applied to force cover 19 through the openings 15 of stent 10.

Figure 13:
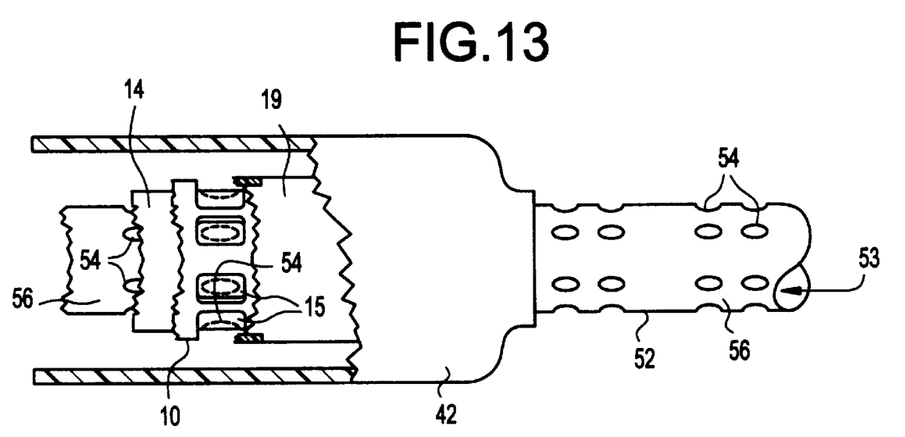
FIG. 13 is a partial cut-away showing the formation of a covered endoprosthesis of the present invention having at least four domains of distinct porosity.
Figure 14:
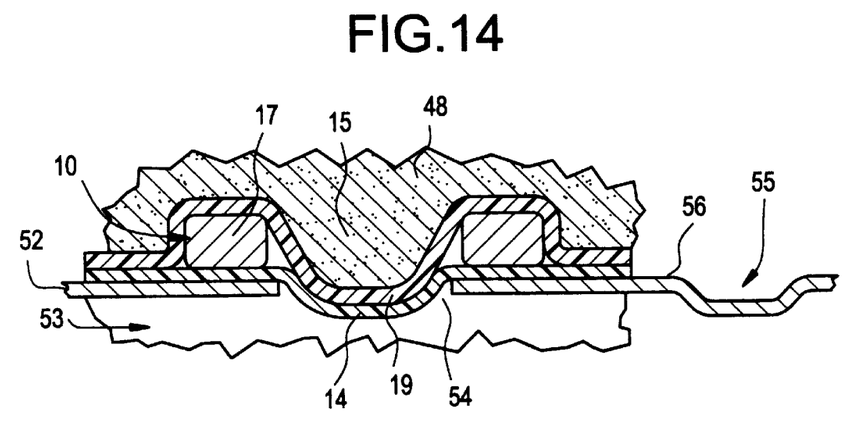
FIG. 14 is a partial cut-away showing the liner and cover of the present invention being forced into an aperture formed in a mandrel.

Furthermore, a fourth domain of distinct porosity 50 may be formed, as shown in FIGS. 13 and 14, by laminating, adhering, or bonding liner 14 to cover 19 within the expanse defined by an aperture 54 formed in the surface 56 of a hollow mandrel 52 having an elongate cavity 53 therethrough. Fourth domain of porosity 50 exhibits a porosity between that of the second domain of porosity 32 and the third domain of porosity 34 due to the bulk density provided by the attached liner 14 and cover 19 which are able to deflect towards cavity 38 as cover 19 is compressed through the openings 15 of stent 10.

With additional reference to FIG. 14, the prosthesis 20 may be formed on a hollow mandrel 52 having apertures 54 formed in a pattern through the surface 56 thereof. Stent 10 is positioned on mandrel 52 so that a portion of openings 15 of the stent are in registry with at least a portion of the apertures 54 of mandrel surface 56. Apertures 54 are desirably formed in communication with elongate cavity 53 although the present invention also contemplates providing a pattern of depressions 55 on the surface of a mandrel. Where cover 19 is forced through an opening 15 in stent 10 that is in registry with an aperture 54 of mandrel surface 56, cover 19 and liner 14 will be compressed to a lesser extent than where the cover 19 and liner 14 are forced against mandrel surface 56. The lower compression between the liner and cover at these locations will result in a device of the present invention having fourth domain of distinct porosity 50 shown in FIG. 9.

In order to function effectively as an endoprosthesis, the inner and outer tubular liners 14 and 19 are laminated together through the open construction of stent 10 so as to form an ePTFE covered composite endoprosthesis 20. As mentioned above, numerous techniques may be employed to laminate or bond inner tubular liner 14 to outer tubular liner 19 through the open spaces 15 of stent 10. Heat setting, adhesive welding, application of uniform force and other bonding techniques may all be employed to bond or secure the inner liner 14 to the outer liner 19 through stent 10. In each of these bonding technique, it is contemplated that liners 14 and 19 be adhered at a location coextensive with the interior surface 11 of stent 10. This is especially beneficial for maintaining the smoothness of inner luminal surface 14d so as to minimize the turbulence of or the interference with fluid flowing through the device while also minimizing the risk of thrombus formation.

In one embodiment, stent 10 may be formed of a shape memory alloy and deliverable within the body at a first diameter, i.e., a contracted diameter, and then expanded to an enlarged diameter once the stent reaches its austenitic start temperature. The particular alloy chosen for the stent is desirably selected to have an austenitic start temperature which is about body temperature, or about 37° C. Stent 10 may therefore be provided having a first diameter so as to fit over liner 14 on mandrel 38. Stent 10 may then be cooled to a fully martensitic state so as to reduce in diameter and to thereby engage liner 14 on mandrel 38. Cover 19 may then be applied to outer surface 13 of stent 10 while maintaining stent 10 below the austenitic start temperature of the stent alloy. Both cover 19 and liner 14 are preferably formed of ePTFE. Cover 19 may then be compressed through the openings 15 of stent 10 and simultaneously heated to a temperature of about 250° C. so as to heat shrink the both liner 14 and cover 19 to be taut about stent 10. While it is desirable to heat shrink the ePTFE material, it is preferred to not sinter the material by heating to a temperature above about 327° C. Furthermore, stent 10 should not be heated to a temperature which may reset the shape memory state of the alloy.

As stent 10 is being heated above its austenitic start temperature, the compressive force forcing cover 19 through the openings 15 will also need to counteract the outward force exerted by stent 10 attempting to achieve its expanded austenitic diameter. Stent 10 may then be cooled back to a martensitic state prior to releasing the compressive force. The method of the present invention may therefore be employed to eliminate any slack in the stent covers as the diameter at which the device is formed is smaller than the nominal diameter at which the device is deployed within a body vessel, i.e., expansion of the device will require expansion of the ePTFE laminated liner and cover.

While the method for forming a composite endoluminal device of the present invention has been described generally, the following is a detailed description of the one preferred method contemplated by the present invention.

With reference to FIGS. 7, 10, and 11, an elongate mandrel 38 is provided and a liner 14 is positioned on mandrel 38. Thereafter, an elongate expandable stent 10 is positioned over liner 14. Stent 10 has an open structure defined by stent segments 17 and openings 15 therebetween and includes an inner stent surface 11 and an outer stent surface 13. Cover 19 is positioned over outer stent surface 13 to thereby form a stent assembly 40 on mandrel 38. Stent assembly 40 is then centered within an open expanse 46 of a radially contractible sleeve 42 such that both ends of sleeve 42 extend over mandrel 38 clear of stent 10 to form a pocket 44. One end of radially contractible sleeve 42 is contracted about mandrel 38 adjacent one end of stent 10. Mandrel 38 is then oriented so that the open end 47 of sleeve 42 opens upward. Pocket 44 is then filled with a flowable mass particulate 48. Sleeve 42 is then radially contracted against flowable mass particulate 48 to push cover 19 into contact with liner 14 through openings 15 in stent 10 at a location coextensive with inner stent surface 11. Cover 19 is then laminated to liner 14 at said location coextensive with said inner stent surface 11.

The radially contractible sleeve 42 may be formed of a heat-shrinkable material. Heat is applied to one end of said heat-shrinkable sleeve 42 to shrink that end of sleeve 42 to the diameter of mandrel 38 so as to form pocket 44 between cover 19 and heat-shrinkable sleeve 42. Once pocket 44 is sufficiently filled with flowable mass particulate 48, heat may then be provided to heat-shrinkable sleeve 42 to compress flowable material 48 against cover 19. An additional compressive force is also contemplated to act upon sleeve 47 to increase the compaction of flowable mass particulate 48 towards the mandrel so as to force cover 19 through openings 15 in stent and into contact with liner 14.

In the present invention, the liner and cover may be formed from a material selected from the group consisting of fluoropolymers, polyimides, silicones, polyurethanes, polyurethane ethers, polyurethane esters, polyurethaneureas and mixtures and copolymers thereof. Additionally, the liner and said cover may be formed from ePTFE. Also, said heat-shrinkable sleeve may be formed from ePTFE. When the liner and cover are formed of ePTFE the heating step desirably includes heating said stent assembly at a temperature below the sintering temperature of the liner and cover, or below about 327° C.

The stent of the present invention may be formed of a shape-memory alloy having a parent diameter corresponding to liner 14 positioned on mandrel 38. The heating step would heat the stent at a temperature below that temperature used to set the shape memory of the stent. Further, said heating step may include applying a compressive force to sleeve 42 to maintain said stent at said parent diameter during said heating step. The stent is then cooled to a martensitic state and the compressive force is then removed.

Figure 12:
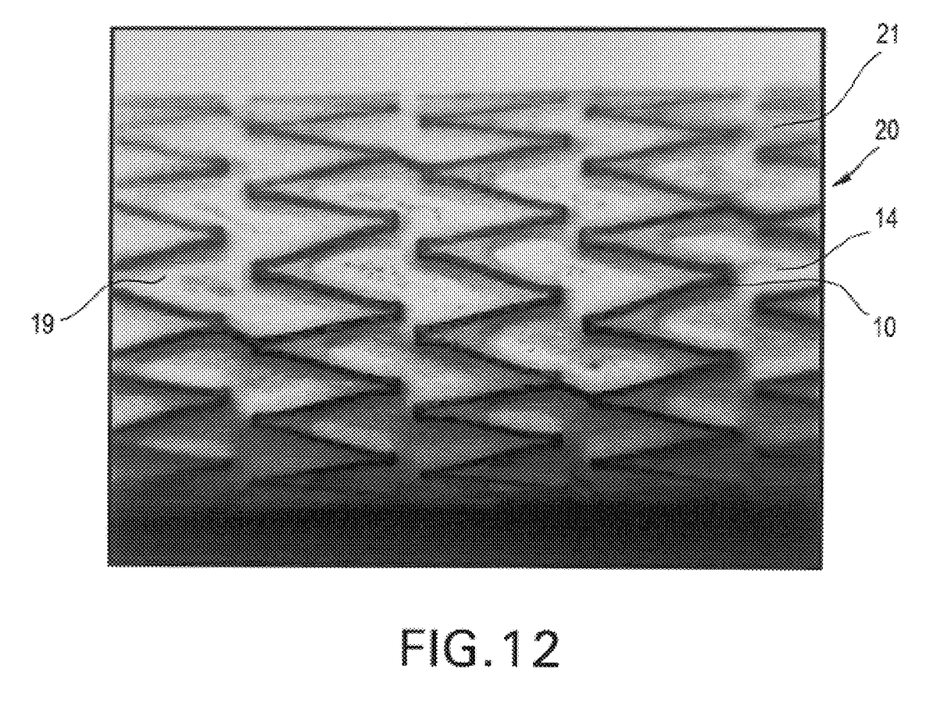
FIG. 12 is a photograph of a portion of an embodiment of assembled covered endoprosthesis of the present invention.

As shown in FIG. 12, a resultant composite endoprosthesis 20 wherein a stent 10 is encased within a polymeric material 21 such as ePTFE may be provided. The coating of polymeric material formed by liners 14 and 19 encloses the body of the stent and also fills the spaces therebetween. Such a device exhibits substantial benefits in endovascular use as the entire stent is covered with a biocompatible thrombus inhibiting material. Furthermore, as the inner luminal surface of the endoprosthesis is formed against a smooth mandrel, the inner luminal surface of the composite endoprosthesis exhibits a relatively smooth configuration mitigating against thrombus formation during use.

Figure 15:
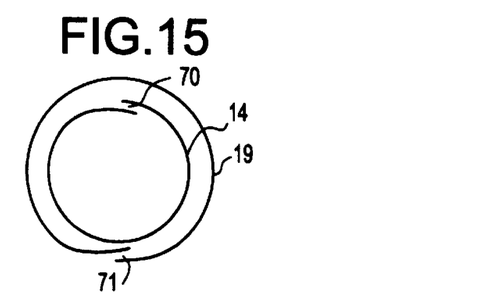
FIGS. 15–21 provide schematic representations of various further embodiments of the liner and cover of the present invention.

It is contemplated that the formation of the liner 14 and the cover 19 may be accomplished by a variety of techniques. A preferred embodiment provides the inner liner and outer cover to each include a longitudinally overlapped seam. The overlapped seam is adheringly closed during the heat-shrink process which secures the outer cover 19 to the inner liner 14 about the stent 10. In one embodiment, it is contemplated that the overlapped seams of the inner liner 14 and the outer cover 19 are circumferentially aligned. It is further contemplated that the present invention may include the seam of the inner liner being rotationally offset with respect to the seam of the outer liner. In one embodiment shown schematically in FIG. 15, an inner liner 14 and outer liner 19 are to positioned about a stent 10 which is for clarity is not shown. Liner 14 includes an overlapped seam 70 while liner 14 includes an overlapped seam 71. The seams 70 and 71 are non-aligned and are preferably rotated 180° with respect to each other.

In each of the above-referenced embodiments, each seam is formed by joining the outer surface of one edge of the sheet with the inner surface of the opposed edge of the sheet. However, it is further contemplated that a tubular structure can be formed from a sheet by joining abutted respective inner surfaces of the opposed edges of the sheet.

Figure 16:
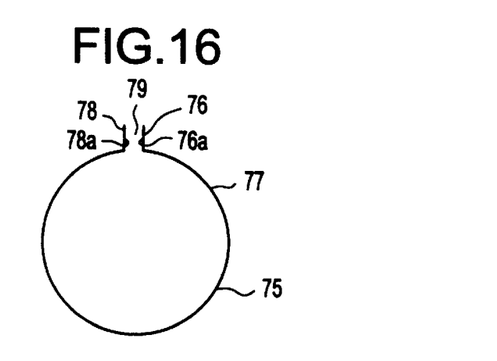

Referring now to FIG. 16, a sheet 75, which may be used to form a tubular structure 77 forming either the inner liner 14 or the outer cover 19, or both, includes opposed edges 76 and 78. The respective inside surfaces 76a and 78a are placed in juxtaposition and are adhered together. The seam 79 formed by such abutment extends radially outward from the tubular structure 77. Once so formed, the seam 79 may be trimmed close to the circumference of the tubular structure 77 to provide a low profile for implantation purposes.

It is further contemplated that the tubular structure may be formed from a sheet where the opposed edges of the tubular structure are brought into close proximity but are not physically joined together.

Figure 17:
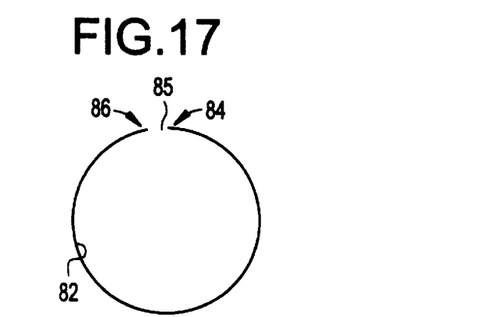
Figure 18:
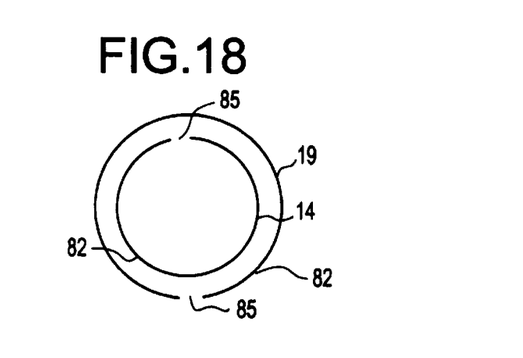
Figure 19:
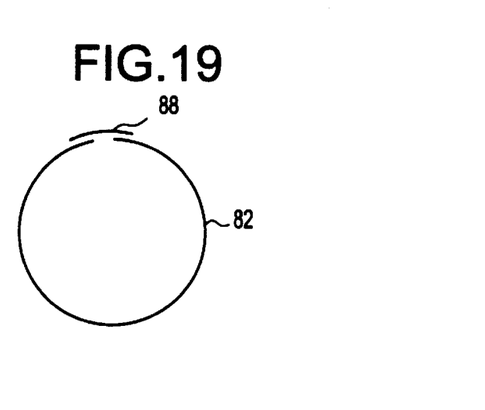

Referring to FIG. 17, a sheet 80 forming the tubular structure 82 may be formed into a tubular configuration by moving the respective opposed edges 84 and 86 into close proximity. Such placement forms a gap 85 therebetween. An inner liner 14 and outer cover 19 may be formed by tubular structure 82 and secured on either side of the stent (not shown) to form a composite structure. It is contemplated that the gap 85 of each of the tubular structures forming the liner 14 and cover 19 may be preferably positioned at different rotational orientations in a manner shown in FIG. 18. As additionally shown in FIG. 19, it is further contemplated that additional strip 88 of ePTFE material may be used to close the gap 85 in outer structure 82.

Figure 20:
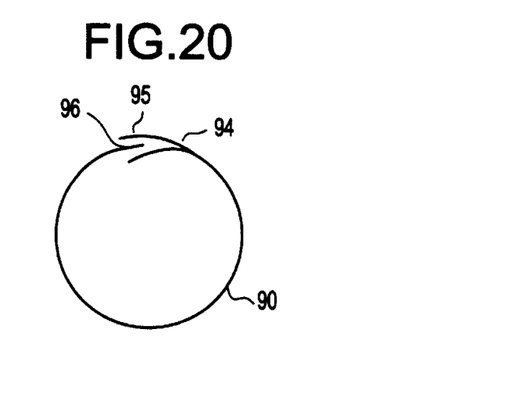

It is further contemplated that in certain embodiments of the present invention, either the liner 14 or the cover 19 or both may be formed of multiple plies of ePTFE sheets. In such an embodiment, the seam may be formed by interposing one edge between the plies of the opposed edge. Referring to FIG. 20, a two-ply sheet 90 of ePTFE may be used to form a tubular structure 92 forming either the liner 14 or the cover 19. Two-ply sheet 90 includes a first opposed edge 94 and a second opposed edge 96. Edge 94 may be split as between the two plys and the opposed edge 96 may be inserted therebetween to form a joined seam 95.

Each of the above-identified embodiments forms a tubular structure by forming a single or multi-ply sheet of ePTFE into a tubular configuration. It is further contemplated that the tubular configuration forming the inner liner 14 or the outer cover 19 may be formed by use of multiple sheet segments.

Figure 21:
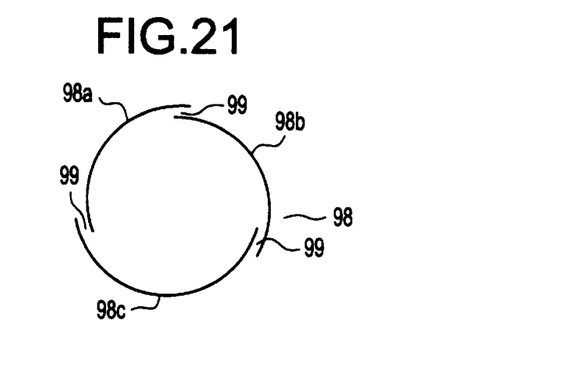

Referring to FIG. 21, a tubular structure 98 used to form either the inner liner 14 or the outer cover 19 is shown. Tubular structure 98 is formed of multiple segments 98a, 98b and 98c of ePTFE material. In the present illustrative embodiment, three segments are used to form the tubular structure 98, each segment extending approximately 120° around the cross-sectional circumference thereof. However, other combinations and numbers of segments may be employed. Each of the segments are interleaved to form overlapped seams 99 along the circumference of the tubular structure 98.

Various changes and modifications can be made to the invention, and it is intended to include all such changes and modifications as come within the scope of the invention as is set forth in the following claims.

What is claimed is:

1. A composite intraluminal device comprising:
    an elongate expandable stent having an open-construction tubular body defined by stent segments and openings between said stent segments, said tubular body defining a generally cylindrically shaped inner surface and an opposed outer surface;
    a first polymeric liner positioned about said inner surface of said tubular body; and
    a second polymeric liner positioned about said outer surface of said tubular body;
    wherein said first liner and said second liner are adheringly joined at a location at or within said inner surface of said tubular body.

2. An intraluminal composite device of claim 1 wherein said first liner defines a fluid contacting luminal surface.

3. The device of claim 1, wherein said device is deliverable through a body lumen.

4. A composite device of claim 1, wherein said stent segments includes opposed inner and outer segment surfaces defining said inner and outer surfaces of said tubular body and opposed side segment surfaces between said inner and outer segment surfaces.

5. The composite device of claim 4, wherein said second liner is conformed to at least a portion of said side segment surfaces.

6. A composite device of claim 1 wherein said first and second polymeric liners enclose said stent segments.

7. A composite device of claim 1 wherein said first and second polymeric liners are formed from materials selected from the group consisting of fluoropolymers, polyimides, silicones, polyurethanes, polyurethane ethers, polyurethane esters, polyurethaneureas and mixtures and copolymers thereof.

8. A composite device of claim 7 wherein said first and second liners are formed from ePTFE.

9. A composite device of claim 1 wherein said expandable stent is formed from nitinol.

10. An intraluminal prosthetic device comprising:
    an elongate tubular polymeric liner;

an elongate tubular stent disposed over said liner, said stent including a generally cylindrical inner stent surface and an outer stent surface, said stent having an open construction defined by stent segments and spaces therebetween; and a polymeric cover disposed over said stent and adhered to said liner through said spaces between said stent segments at a location at or within said inner stent surface;

said liner, stent, and cover providing at least three domains of distinct porosity at locations along the length thereof.

11. The device of claim 10, wherein said three domains of porosity include a first domain of porosity formed by a stent segment between said liner and cover and having a first porosity.

12. The device of claim 11, wherein said three domains of porosity include a second domain of porosity formed by said liner and cover adjacent to a stent segment and having a second porosity greater than said first porosity.

13. The device of claim 12, wherein said three domains of porosity include a third domain of porosity formed by said liner adhered to said cover between adjacent stent segments and having a third porosity between said first and second porosities.

* * * * *

UNITED STATES PATENT AND TRADEMARK OFFICE
CERTIFICATE OF CORRECTION

PATENT NO. : 6,139,573
DATED : October 31, 2000
INVENTOR(S) : Sogard et al.

It is certified that error appears in the above-identified patent and that said Letters Patent is hereby corrected as shown below:

Column 8,
Line 20, the printed patent incorrectly reads ", Figure 1 shows a stent which"; the patent should read -- , Figure 1 shows stent 10 which --.

Column 12,
Line 12, the printed patent incorrectly reads "an air gap-between ..."; the patent should read -- an air gap between --.

Column 12,
Line 24, the printed patent incorrectly reads "so as to force-cover 19. ."; the patent should read -- so as to force cover 19 --.

Column 14,
Line 45, the printed patent incorrectly reads "15 in stent and into . ."; the patent should read -- 15 in stent 10 and into --.

Signed and Sealed this

Sixth Day of November, 2001

*Attest:*

*Attesting Officer*

NICHOLAS P. GODICI
*Acting Director of the United States Patent and Trademark Office*